US00PP30048P2

(12) United States Plant Patent
Hansen

(10) Patent No.: US PP30,048 P2
(45) Date of Patent: Jan. 1, 2019

(54) ***DIANTHUS* PLANT NAMED 'CLASSIC CORAL'**

(50) Latin Name: ***Dianthus* hybrid**
Varietal Denomination: Classic Coral

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/932,094

(22) Filed: Feb. 1, 2018

(51) Int. Cl.
*A01H 5/02* (2018.01)

(52) U.S. Cl.
USPC ..... Plt./281
CPC ..... *A01H 5/02* (2013.01)

(58) Field of Classification Search
USPC ..... Plt./181, 276
CPC ..... A01H 5/02
See application file for complete search history.

*Primary Examiner* — Kent L Bell

(57) ABSTRACT

A new and unique plant cultivar of perennial carnation or pinks, *Dianthus* plant named 'Classic Coral' with numerous, large, fully-double, lightly-fragrant flowers producing a rounded full face. The numerous stems cover top to bottom of clump on well-branched stems having up to 11 flowers per stem. Petals are coral pink and have fine serrations. The habit is compact with long blue-green foliage.

1 Drawing Sheet

Botanical denomination: *Dianthus* hybrid.
Cultivar designation: 'Classic Coral'.

BACKGROUND OF THE INVENTION

The present invention relates to the new and distinct cultivar of carnation or pinks from the genus *Dianthus* and given the cultivar name 'Classic Coral'. The new plant was the result of an intentional cross on Jun. 14, 2012 under the direction of the inventor between *Dianthus* 'Double North' (not patented) as the female or seed parent and an individual yellow-flowering selection of the 'Lillipot' strain (not patented) as the male or pollen parent. The cross was harvested and sown on Jul. 2, 2012. The new hybrid was first isolated from trials at a wholesale perennial nursery in Zeeland, Mich. during the summer of 2013 as a single seedling clone and given the breeder number 12-84-4 later in the evaluation processes. *Dianthus* 'Classic Coral' has been asexually propagated at the same nursery in Zeeland, Mich. since 2013 using traditional shoot tip cutting procedures and found to reproduce plants that are identical and exhibit all the characteristics of the original plant.

No plants of *Dianthus* 'Classic Coral' have been sold in this country, or anywhere in the world, under this or any name or tradename, prior to the filing of this application, nor has any disclosure of the new plant been made prior to the filing of this application with the exception of that which was disclosed or sold within one year of the filing of this application and was either derived directly or indirectly from the inventor.

SUMMARY OF THE INVENTION

*Dianthus* 'Classic Coral' has not been evaluated under all possible environmental conditions. The phenotype may vary with variations in environment including: growing temperature, available sunlight, nutrients, water, etc. without a change in the genotype of the plant.

Compared with the new plant, the female parent 'Double North' has pure white flowers with fewer petals and the panicles are semi-drooping, whereas the new plant has coral pink petals that are more numerous per flower and the panicles are nearly vertical. Compared with 'Classic Coral' the male parent has nearly solid pale creamy yellow flower petals and the flowers of the new plant have not been observed to produce stamens. The nearest comparison cultivars known to the inventor are: 'Coral Reef' U.S. Plant Pat. No. 19,660 and 'Stardust' U.S. Plant Pat. No. 20,999. The flower petals of 'Coral Reef' are primarily a lighter reddish coral color with fewer petals than the new plant. Compared with 'Stardust', the new plant has over twice as many petals per flower and over twice as many flowers per panicle and stamens have not been observed in the flowers of 'Classic Coral'.

*Dianthus* 'Classic Coral' is distinct from its parents and all other *Dianthus* known to the applicant in the following combined traits:

1. Fully-double flowers opening up with a full and rounded face.
2. Petals having a coral pink coloration with faint bar near the base of the petal limb.
3. Petal margin irregularly toothed.
4. Multiple flowers per stiff, upright peduncle.
5. Large flower size producing a lightly-sweet spicy fragrance.
6. Flower coverage top to bottom of clump, vigorous, with compact habit and blue-green foliage.

BRIEF DESCRIPTION OF THE DRAWINGS

The photographs of the new invention are of a two-year-old plant grown in full-sun trial garden and demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
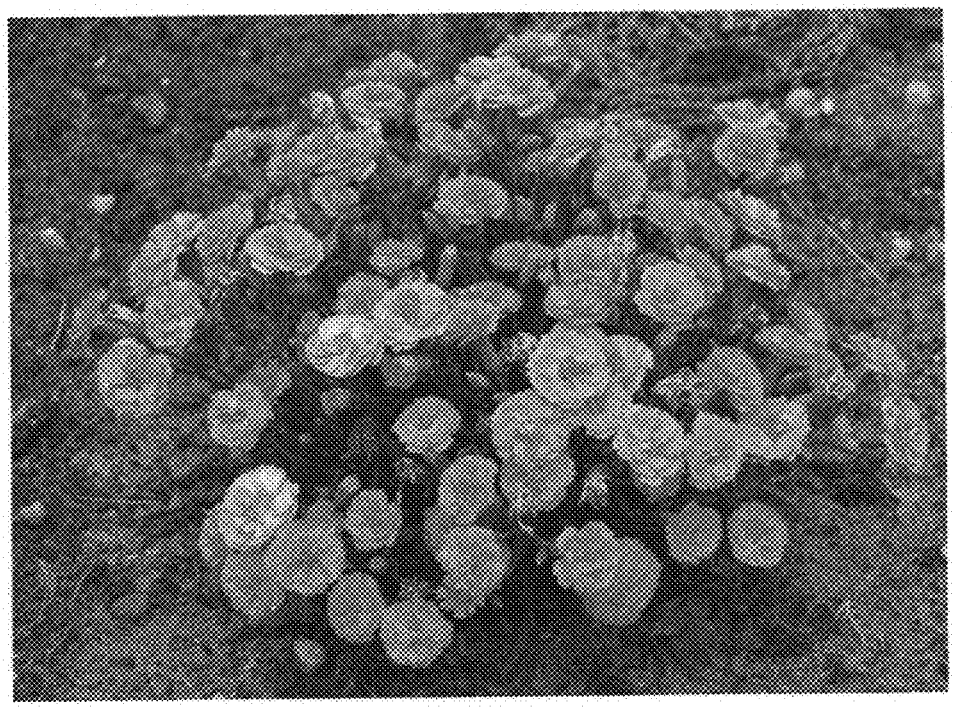
FIG. 1 shows the habit of the plant in mid-season flowering.
Figure 2:
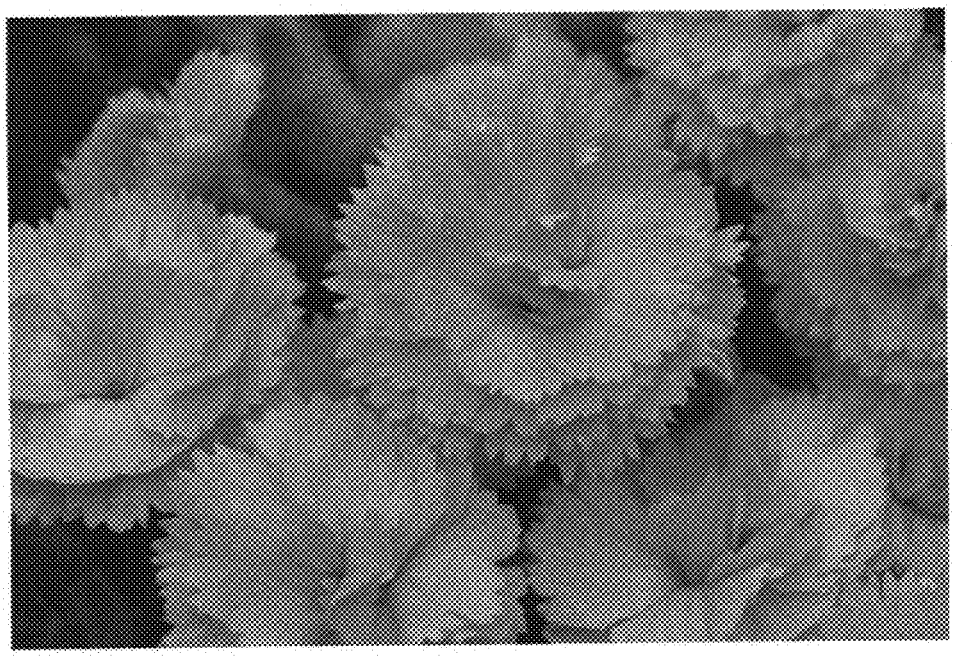
FIG. 2 shows a close-up of the flowers and bud.

The following detailed description of the new plant is based on observations of one-year-old plants in greenhouse-grown containers in addition to two-year-old plants in full-sun trial garden at a nursery in Zeeland, Mich. with supplemental watering, light additions of fertilizer and free of other plant growth regulators. All color usage is in accordance with the 2015 edition of The Royal Horticultural Colour Chart except where common dictionary terms are used.

Botanical classification: *Dianthus* hybrid;

Parentage: *Dianthus* 'Double North' as the female or seed parent, and as the male or pollen parent an individual yellow-flowering selection of *Dianthus caryophyllus* 'Lillipot' yellow strain;

Plant habit: Caespitose, herbaceous, evergreen, winter-hardy perennial; stems and peduncles branched, mostly erect stems; height of foliage about 15.0 cm and about 36.0 cm across; height in flower is about 25.0 cm;

*Root system*.—Fine, fibrous; color nearest RHS 155D.

*Vigor*.—Good, spring planted plugs finish in 3.8 liter pots in seven to eight weeks.

Foliage:

*Leaf type*.—Simple, linear, opposite, decussate, sessile, glabrous, glaucous both adaxial and abaxial; margin entire to microscopically serrulate; acute apex; base decurrent, adpressed along stem to slightly perfoliate; no fragrance detected.

*Leaf dimensions*.—To about 9.0 cm long and about 7.0 mm wide, average about 8.5 cm long and 5.0 mm wide.

*Leaf color*.—Young expanding leaves abaxial nearest RHS 137B and adaxial nearest RHS 137A; mature abaxial nearest RHS N138B and adaxial blend between RHS N138A and RHS 189A.

*Venation*.—Not pronounced; obscurely pinnate, coloration same as that of leaf top and bottom.

Stems: About 52 per plant; upright; terete, glabrous, glaucous; solid; branching in upper nodes;

*Stem size*.—About 20.5 cm long to peduncle and about 3.0 mm wide at base.

*Stem color*.—Nearest RHS 122A.

*Branching*.—Numerous; typically alternate from upper nodes; about 4 per main stem and about 200 per plant; branch size average about 7.0 cm long and 1.0 mm diameter at time of initial flowering.

*Nodes*.—About 3.5 mm across; color nearest RHS 145D.

*Internodes*.—About 11 per stem before peduncle; average about 1.9 cm apart depending on growing temperature, shorter in cooler conditions.

Inflorescence:

*Type*.—Terminal, cymose; perfect; salverform; actinomophic; fully double.

*Attitude*.—Upright to slightly outward around perimeter of plant.

*Dimension*.—About 4.6 cm across and extending about 4.6 cm above base of calyx tube and 1.4 cm wide at apex of calyces.

*Flowers per stem*.—Up to 11, average 9.

*Pedicel*.—Glaucous, glabrous, terete, stiff; primarily upright.

*Pedicel size*.—Terminal flower about 2.0 mm long and about 2.5 mm diameter; other flowers average about 4.0 mm long and 2.0 mm diameter.

*Pedicel color*.—Nearest RHS 189B.

*Flower bud*.—Slowly opening; glabrous; glaucous; with calyx still closed: ellipsoid with rounded base and apex; about 3.2 cm long and 1.2 cm across at distal fusion point of sepals; with petals extended beyond calyx and still parallel to calyx side: terete, with rounded base and truncate apex or petal tops, about 3.2 cm long and 1.2 cm across near apices of petals.

*Flower bud color*.—With petals enclosed in calyx distally between RHS 160D and RHS 158D, mid portion between RHS 146A and RHS 146B and base nearest RHS 146D; with petals extended beyond calyx petal portion lighter than RHS 58D.

*Flower period*.—Beginning late spring and continuing for about six weeks.

*Flower fragrance*.—Light, sweet spicy, clove-like.

*Flower lasting quality*.—Individually about seven to ten days on or cut from plant.

*Petals*.—Glabrous; up to about 51 per flower, average about 47; consisting of a rounded blade or limb and a claw; limb and claw combined are flabellate; limb apex and margin with fine irregular dentations average 1.5 mm wide and 1.0 mm long; limb bent outwardly in distal 16.0 mm to nearly a ninety degree angle creating a full rounded face; persistent.

*Petal dimensions*.—Limb to about 22.0 mm across, average about 20.0 mm across; claw tapering to attenuate base of about 1.0 mm across; whole petal to about 43.0 mm long, average about 40.0 mm long.

*Petal color*.—Young abaxial claw nearest RHS 145D, young abaxial limb center between RHS 55B and RHS 55C with limb perimeter between RHS 55B and RHS 54B; young adaxial claw nearest RHS 145D, young adaxial limb between RHS 55A and RHS 54A; mature abaxial claw nearest RHS 145D, between base of limb and distal claw lighter than RHS 55D, limb between RHS 55C and RHS 55D; mature adaxial claw nearest RHS 145D, between base of limb and distal claw lighter than RHS 55D, limb distally between RHS 55B and RHS 55C with faint bar near base of limb nearest RHS 55B.

*Calyx*.—Glabrous; glaucous abaxial; margins entire to micro-ciliolate; consisting of five sepals with acute apex and fused base forming five-toothed corolla tube fused in about proximal 17.0 mm; campanulate to about 20.0 mm long and about 19.0 mm in diameter at apex.

*Sepals*.—Individually about 23.0 mm long and about 6.0 mm across at distal fusion.

*Sepal color*.—Abaxial margin between RHS 160D and RHS 158D, mid-portion between RHS 146A and RHS 146B, base nearest RHS 146D; adaxial margin between RHS 160D and RHS 158D, mid-portion between RHS 147B and RHS 147C, base between RHS 147C and RHS 147D.

*Peduncle*.—Glabrous, glaucous, terete, stiff; about 10.0 cm long and about 3.0 mm diameter at base; attitude mostly upright.

*Peduncle color*.—Blend between RHS 122A and RHS 189B.

*Epicalyx*.—Two pairs subtending each flower; opposite, glaucous, glabrous; sessile, margin entire, broadly lanceolate with broadly acute apex and cuneate base; outer pair about 7.0 mm long and about 5.0 mm wide, inner pair about 10.0 mm long and about 7.5 mm across.

*Epicalyx color*.—Both pairs abaxial base nearest RHS 146D, mid-portion between RHS 136A and RHS 137A, margin translucent to nearest RHS 158D; adaxial base nearest RHS 146D, mid-portion nearest RHS 137B, margin translucent to nearest RHS 158D.

*Androecium*.—Not observed.

*Gynoecium*.—Single. Pistil: to about 13.0 mm long. Style: bifurcate just above ovary; to 5.0 mm long; color nearest RHS 155D with tint of nearest RHS 145D toward base. Stigma: slightly flattened abaxial to adaxial; puberulent; about 2.5 mm long and 1.0 mm wide; color nearest RHS N155D. Ovary: superior; ellipsoid-shaped with broadly acute apex and truncate base; about 7.0 mm long and 5.5 mm wide; color nearest RHS 145B.

Fruit: Not observed;

Disease resistance: The new plant is resistance to center die out from fungus or high temperatures. The plant grows best with adequate moisture and well-drained soil, but is able to tolerate some drought once established. Hardiness at least from USDA zone 4 through zone 9.

It is claimed:

1. A new and distinct *Dianthus* plant named 'Classic Coral' essentially as herein described and illustrated.

* * * * *